(12) United States Patent
Luitjes et al.

(10) Patent No.: US 6,355,713 B1
(45) Date of Patent: Mar. 12, 2002

(54) β-KETOESTERS FOR USE AS POLYMER STABILIZERS

(75) Inventors: Hendrikus Luitjes, Putten; Jacco Van Haveren, Ede; Augustinus Emmanuel Frissen, Wageningen; Gerard Hubert Schmets, Horn; Frans Jeanette Maria Leonardus Peters, Eygelshoven; Erica Gertruda Arnolda Kroon; Johannes Albertus Van Der Waal, both of Roermond, all of (NL)

(73) Assignee: Akcros, Chemicals, Manchester (GB)

( * ) Notice: Subject to any disclaimer, the term of this patent is extended or adjusted under 35 U.S.C. 154(b) by 0 days.

(21) Appl. No.: 09/424,633

(22) PCT Filed: May 27, 1998

(86) PCT No.: PCT/NL98/00307
    § 371 Date: Jan. 7, 2000
    § 102(e) Date: Jan. 7, 2000

(87) PCT Pub. No.: WO98/54246
    PCT Pub. Date: Dec. 3, 1998

(30) Foreign Application Priority Data

May 27, 1997 (EP) ............................ 97201606

(51) Int. Cl.$^7$ ................................. C08K 5/10
(52) U.S. Cl. ....................... 524/317; 560/172; 560/174; 560/178
(58) Field of Search ................... 524/58, 317; 560/172, 560/174, 178

(56) References Cited

U.S. PATENT DOCUMENTS 3,346,536 A    10/1967  Kauder et al.
5,064,925 A *  11/1991  Hannaby ...................... 528/44
5,098,984 A *   3/1992  Mafoti ......................... 528/73
5,840,703 A *  11/1998  Corrigan ...................... 514/23
5,965,767 A *  10/1999  Sivik .......................... 560/126
6,057,001 A *   5/2000  Schoonderwoerd ...... 427/385.5
6,121,440 A *   9/2000  Kenneally .................... 536/115
6,222,062 B1 *  4/2001  Anderson .................... 560/174

FOREIGN PATENT DOCUMENTS

EP    0 599 478        6/1994
GB    2046091      *  11/1980
JP    06 065458        3/1994

* cited by examiner

Primary Examiner—Paul R. Michl
(74) Attorney, Agent, or Firm—Young & Thompson

(57) ABSTRACT

β-Ketoesters and their enamines derived from alcohols or polyols are suitable for stabilizing polymers, and are represented by formulae: $A[(O-CHR^4-Z-CHR^5)_m-O-CO-CHR^1-CO-R^3]_n$ and $A[(O-CHR^4-Z-CHR^5)_m-O-CO-CR^1=C(-NHR^2)-R^3]_n$, wherein: A is the residue of an alcohol or polyol selected from hydroxyalkanoic acid esters, sugars and their glycosides, sugar alcohols, sugar acids and their esters, and oligosaccharides; m is an integer number from 0 up to 6; n is a number from 1 up to the total number of hydroxyl groups in the polyol; $R^1$ is hydrogen, $C_1$–$C_8$ alkyl, $C_3$–$C_8$ alkenyl or cycloalkyl (alkyl) or $C_6$–$C_8$ aryl or aralkyl; $R^2$ is hydrogen, $C_1$–$C_6$ alkyl, $C_2$–$C_6$ hydroxyalkyl or $C_3$–$C_6$ alkenyl; $R^3$ is $C_1$–$C_{18}$ alkyl, alkoxy or alkylamino, $C_3$–$C_{18}$ alkenyl, alkanoylmethyl, alkoxycarbonylmethyl or cycloalkyl(alkyl), $C_6$–$C_{18}$ aryl, aryloxy, arylamino, aralkyl, aralkoxy or aralkylamino, or $C_8$–$C_{18}$ aroylmethyl, aryloxycarbonylmethyl or arylcarbamoylmethyl; $R^4$ and $R^5$ are independently hydrogen or methyl; and Z is a direct bond, $CH_2$, CHOH, $CH-O-CO-CHR^1-CO-R^3$ or $O-CO-CR^1=C(-NHR^2)-R^3$.

15 Claims, No Drawings

β-KETOESTERS FOR USE AS POLYMER STABILIZERS

The present invention pertains to the use of β-ketoesters and their enamines for stabilising thermoplastic polymers.

The use of β-ketoesters for stabilising polymers, especially vinyl chloride polymers, is known in the art. EP-A-433230 discloses alkylene and alkylenoxy β-ketoesters such as butanediol bis-benzoylacetate and trimethylolpropane tris-acetoacetate, as stabilisers for chlorine-containing polymers. Similarly, JP-A-6-65458 (Chem. Abstr. 121 (1994) 135609t) describes a combination of ethyleneglycol diacetoacetate, a metal alkanoate and a phenolic antioxidant to be used for thermal stabilisation and colour protection in PVC.

Alkanolamide β-ketoalkanoates such as tris-acetoacetoxyethyl isocyanurate as stabilisers for chlorine-containing polymers are described in EP-A-22749. β-Ketones constitute another group of useful stabilisers. An effective but expensive β-ketone stabiliser is stearoyl benzoyl methane, commercially available as Rhodiastab 50®.

Mixtures of stabilisers containing at least a disaccharide alcohol such as maltitol or isomaltitol and a zinc compound (zinc stearate) are disclosed in EP-A-677549. These mixtures result in improved heat stability of polyvinyl-chloride compositions.

EP-A-599478 discloses the use of acetoacetate esters and their enamines, including sorbitol acetoacetate and trimethylolpropane acetoacetate, as a coalescent in water-based acrylic polymers.

EP-A-114270 describes isosorbide mono-acetoacetate and isosorbide mono-β-amino-crotonate as intermediates in the preparation of isosorbide dihydronicotinate derivatives as anti-hypertensive drugs.

It was found that specific β-ketoesters and their enamines, which can be obtained from inexpensive natural raw materials, have improved stabilising capacities for use in thermoplastic polymers such as PVC. These β-ketoesters not only improve the initial colour stability of polymers, but also increase the thermal stability of the polymers. They can be used in rigid polymers, and they are also effective in stabilising flexible polymers. They have an improved performance to cost ratio. The β-ketoesters and their enamines to be used according to the invention are derived from alcohols or polyols which are natural products or can be obtained from natural products by reduction or chemical and fermentative processes. They are defined in the appending claims. It may be noted that although the β-keto-esters and the corresponding amines are represented in the formulae 1 and 2 as diketo compounds and keto-enamines respectively, they can also exist in their tautomeric forms of keto-enols and ketoimines, respectively, as in formulae 1a and 2a given below. All these and other tautomeric forms are understood to be included in the formulae used.

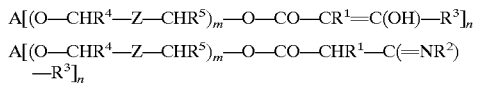

The group A in the ketoester and enamine thereof according to the invention may be substituted by an aryl group, in particular phenyl, benzyl or phenethyl, which is optionally substituted by hydroxy and/or $C_1$–$C_4$ alkyl. As an example, one or more free hydroxy groups of the polyol, i.e. hydroxyl groups not esterified with β-keto acid, may be esterified with benzoic acid or with 3-(3,5-di-t-butyl-4-hydroxyphenyl) propanoic acid (antioxidant group), or two of such free hydroxyl groups may be acetalised with a substituted benzaldehyde.

Examples of the β-ketoesters and enamines to be used according to the invention are ketoesters of lactic acid esters, i.e. α-(β-ketoacyloxy)propionic acid esters, such as ethyl, butyl, lauryl, stearyl, and especially phenyl, 3,5-di-t-butyl-4-hydroxybenzyl and 2,2,6,6-tetramethyl-4-piperidyl esters.

A very useful group of β-ketoesters and enamines is derived from sugars, sugar alcohols, dehydrated sugar alcohols and oligosaccharides. These are polyols, which preferably contain more than one β-ketoester or enamine groups. Suitable sugars comprise glucose, galactose, fructose, (iso) maltulose, leucrose, lactose, sucrose, glucose oligomers such as trehalose, maltose, isomaltose, cellobiose, and higher homologues, such as maltotriose and cyclodextrins, fructose oligomers (especially inulin derivatives) and mixed oligomers and mixtures of these sugars, as well as glycosides of reducing sugars. Oligosaccharides are understood as short-chain polysaccharides having an average degree of polymerisation up to 40 monosaccharide units. Suitable sugar alcohols include xylitol, arabinitol, sorbitol, mannitol, galactitol, lactitol, maltitol, isomaltitol, maltotriitol and the like, and dehydration products thereof such as sorbitan, galactitan, isosorbide and other dianhydroglycitols such as isomannide and isoidide. As explained above, part of the polyol hydroxy groups may be free or be esterified or etherified with other groups, such as aryl groups.

β-Ketoesters and their enamines of sugar acids and their esters, i.e. where the β-ketoacyl groups or β-aminocrotonoyl groups are attached to the hydroxy groups of the sugar acids or their esters, are also effective stabilisers according to the invention. Suitable sugar acids include the glyconic, glycuronic and glycaric acids such as gluconic acid, lactobionic acid and the like, and acids which can be obtained by oxidation or fermentation processes from sugars, such as lactic acid, citric acid, malic acid, tartaric acid, gluconic acid, L-ascorbic acid and the like.

The ketoester groups may be aliphatic groups, such as acetoacetyl, pivaloylacetyl, stearoylacetyl or methoxycarbonyl-acetoacetyl (the monoester of 3-oxoglutaric acid), but they may also contain aryl groups, such as in benzoylacetyl and ring-substituted derivatives thereof. The enamines of the ketoesters such as β-aminocrotonates and N-substituted β-aminocrotonates, are equally suitable.

The β-ketoesters can be prepared in a manner known per se, e.g. by reacting the alcohol or polyol, i.e. the hydroxyalkanoic ester, sugar, sugar acid or sugar alcohol, with a lower alkyl ester of the β-ketoacid with or without a transesterification catalyst such as a tetra-alkoxytin. It was found that such a catalyst is not necessary for the compounds of the invention, and that the purity of the products is even higher when a catalyst is not used. The absence of a catalyst has as a further advantage that traces of water do not affect the transesterification efficiency. Instead of using a lower alkyl ester of the β-keto acid, the synthesis can also be performed using a diketene (4-alkylidene-2-oxo-oxetane) with the appropriate alcohol or polyol or dianhydroglycitol. Prior to the reaction of the alcohol or polyol with the β-ketoacid lower alkyl ester or diketene, it may reacted with an epoxide such as ethylene oxide, propylene oxide or glycidol, eventually resulting in a β-ketoacid ester having one or more alkylenoxy groups interposed between the β-ketoacyl group (s) and the alcohol or polyol residue. The β-aminocrotonates can be prepared by simply reacting the β-ketoester with ammonia or with an amine such as methylamine or ethanolamine.

The β-ketoesters and their enamines can be used in polymer compounds in a manner known per se. The stabilisers can be mixed with other additives, such as impact modifiers for rigid formulations (for example chlorinated polyethylene or butadiene/styrene/(acrylonitrile) co- or terpolymers), plasticisers for flexible formulations (for example phthalic esters such as dibutyl phthalate or dioctyl phthalate, aliphatic monobasic or dibasic esters such as butyl oleate, epoxidised soybean oil, dioctyl adipate), fillers, pigments, flow modifiers (for example acrylates), lubricants (for example calcium stearate, zinc stearate, fatty esters and amides), flame retardants (for example aluminium hydroxide, antimony trioxide), phosphites (for example triaryl phosphites or aryl-alkyl phosphites), antioxidants (for example hindered phenols), HALS (hindered amine light stabiliser) compounds, UV absorbers (for example benzophenones such as 2-hydroxy-4-methoxybenzophenone, benzotriazoles, salicylates), other keto esters and ketones such as N-phenyl-3-acetyl-2,4-pyrrolidinedione; other polyol co-stabilisers, such as pentaerythritol, tris (hydroxyethyl)isocyanurate and the like, may also be used at reduced levels. Co-stabilisers and other additives that can be used together with the β-ketoesters of the invention are also mentioned in EP-A-677549.

Preferred combinations of the β-ketoesters and their enamines for use as stabilisers include combinations with polyols such as those described above (including e.g. sorbitol, lactitol and inulin), but also non-sugar polyols such as tris(hydroxyethyl)isocyanurate, (di)pentaerythritol or trismethylolpropane, in a weight ratio of e.g. between 1:10 to 10:1, especially of 1:4 to 4:1. The combination of the β-ketoesters/enamines and polyols, especially sugar alcohols like sorbitol was found to be particularly useful, since it provides an excellent heat stability and colour stability. Other preferred combinations are those with inorganic materials including oxides and mixed oxides of e.g. alkali and alkaline earth metals, aluminium, silicon, titanium, zinc, tin and lead, such as hydro-talcites, silicates, dawsonites, zinc oxide and zeolites, and salts of such metals, especially zinc carboxylate salts (zinc stearate, calcium stearate and the like), and other organo-metal compounds such as stannanes.

The β-ketoesters and their enamines can be used for stabilising thermoplastic polymers. These can be e.g. polyethene, polypropene, polystyrene, a halogenated rubber, fluorine-containing polymers, such as poly(vinylidene fluoride), poly(vinylidene-chloride) and, especially, poly (vinyl chloride). The chlorinated polymers such as PVC, the non-vinyls (polyethene and polypropene) and halogenated rubbers are preferred according to the invention. The β-ketoesters are used at a level of 0.001–5%, especially 0.01–1%, with respect to the thermoplastic polymer.

The heat stability of a polymer like PVC can be expressed in the heating time at a selected temperature (e.g. 200° C.) until the polymer degrades as determined by the colour turning brown to black. The test can e.g. be performed in a Matthis oven using a 25 cm polymer strip which is stepwise moved from the oven.

Non-vinyl polymers as PE are investigated in multi-extrusion tests, after the first, third and fifth run, the colour properties and the melt flow index are measured. Polyolefines are very sensitive to UV-light, therefore UV-stabilising tests are carried out.

The colour properties can be expressed as the whiteness according to Berger (Wb (%)) and the Yellowness index (Yi (%)). Both can be determined e.g. using a Minolta Chromameter with a DP 301 data processor. The rating is done according to the CIE L-a-b system (CIE: Commission Internationale d'Eclairage). White/black (L), green/red (a) and yellow/blue (b) values are converted to the Wb and Yi values. For optimum performance, the heat stability and the whiteness should be as high as possible, and the yellowness index should be as low as possible.

The formulations can be processed into a shaped article by means of calendering, rotational moulding, spread coating, slush moulding, extrusion, injection moulding, blow-moulding or other conventional technique.

In the examples that follow, the synthesis of stabilisers according to the invention and their use in polymer compounds are illustrated. The compounds tested are the PVC compounds A–D obtained from premixed components given below.

| Compound A (Rigid PVC): | | |
|---|---|---|
| Polyvinylchloride | S-PVC (K-68) | 100 parts |
| Impact modifier | acrylate compounds | 2–15 phr |
| Filler | chalk | 2–12 phr |
| Pigment | titanium dioxide | 1–10 phr |
| Flow modifier | acrylate ester homopolymer | 0.1–3 phr |
| Metal stabiliser | calcium/zinc stabiliser | 0.1–5 phr |
| Lubricant | PE wax | 0.01–2 phr |

| Compound B (Rigid PVC): | | |
|---|---|---|
| Compound A + | | |
| Polyol | THEIC | 0–1 phr |
| Polyol | lactone | 0.01–2 phr |
| Polyol | partial ester | 0.01–1 phr |
| Layered clay | anionic clay | 0.01–2 phr |
| Costabiliser | β-diketone | 0.01–2 phr |
| Organic phosphite | organic diphosphite | 0.01–2 phr |

| Compound C (Flexible PVC): | | |
|---|---|---|
| Polyvinylchloride | S-PVC (K-71) | 100 parts |
| Plasticiser | dioctyl phthalate | 10–50 phr |
| Epoxy plasticiser | epoxidised soybean oil | 0.3–10 phr |
| Lubricant | PE wax | 0.01–2 phr |
| Organic zinc salt | liquid zinc stabiliser | 0.01–2 phr |

| Compound D (Rigid PVC pipe formulation): | | |
|---|---|---|
| Polyvinylchloride | S-PVC (K-67) | 100 parts |
| Filler | chalk | 2–10 phr |
| Metal stabiliser | calcium/zinc stabiliser | 0.5–2 phr |
| Acid scavenger | zeolite P | 0.2–3 phr |
| Lubricant | synthetic paraffin | 0.1–2 phr |
| Lubricant | PE wax | 0.01–2 phr |
| Antioxidant | phenolic antioxidant | 0.01–0.5 phr |
| Epoxy plasticiser | epoxidised soybean oil | 0.3–10 phr |
| Polyol | dipentrol | 0–2 phr |
| Additive of the invention | | 0.1–5 phr |

EXAMPLE 1

Synthesis of sorbitol(AcAc)$_3$ and sorbitol(AcAc)$_4$

A mixture of 50 g (275 mmol) sorbitol and 175 ml (1052 mmol) t-butyl acetoacetate was stirred at 130° C. for 3 hours. Simultaneously, 69.9 g of t-butanol (945 mmol) was distilled off. Then residual t-butyl acetoacetate was distilled off at 100° C. and at reduced pressure. The product was obtained as a pale yellow oil. Yield 127.3 g (87%).

$^{13}$C-NMR (DMSO-d$_6$): 30.20 (CH$_3$), 49.6–50.0 (C(=O)CH$_2$), 63.0–63.3 (H$_2$COH, H$_2$COC), 66.4–74.1 (HCOH, HCOC), 166.7–167.7 (C(=O)OC), 201.5–202.1 (CC(=O)C).

EXAMPLE 2

Synthesis of lactitol(AcAc)$_6$

A well-stirred mixture of 9.06 g (25 mmol) of lactitol monohydrate and 33.2 g (32 ml; 255 mmol) of ethyl acetoacetate was heated at 150–160° C. for 3 hours and the ethanol formed during reaction was distilled off. After another 30 minutes at 170–175° C. a total amount of 6.86 g (15 mmol=6 eq) of ethanol was collected. The reaction mixture was cooled to 80–90° C. and unreacted ethyl acetoacetate was distilled off under vacuum. In this way 14.08 g (110 mmol) ethyl acetoacetate was collected. The product was obtained as an almost colourless solid mass. Yield: 17.6 g (83%).

$^{13}$C-NMR (DMSO-d$_6$): 30.10 (CH$_3$), 49.4–49.9 (C(=O)CH$_2$), 60–67 (CH$_2$COH, CH$_2$OC), 67–77 (HCOH, HCOC), 103.4 (OCO), 166.4–167.5 (C(=O)OC), 201.6 (CC(=O)C).

EXAMPLE 3

Synthesis of lactitol(AcAc)$_3$

A well-stirred mixture of 36.23 g (0.1 mol) of lactitol monohydrate and 39.04 g (38 ml; 0.3 mol) of ethyl acetoacetate was heated at 150–160° C. for 3 hours and the ethanol formed during reaction distilled off. After another 30 minutes at 170–175° C., with distilling off the ethanol, the reaction mixture was cooled to room temperature. A slightly yellowish homogeneous mass of crude product resulted. A total amount of 17.5 ml ethanol was collected and 51.94 g (87%) lactitol-tris(acetoacetate) was obtained.

$^{13}$C-NMR (DMSO-d$_6$): 30.25 (CH$_3$), 49.6–50.0 (C(=O)CH$_2$), 60–66 (CH$_2$COH, CH$_2$OC), 66–76 (HCOH, HCOC), 104.7 (OCO), 167.5 (C(=O)OC), 201.9 (CC(=O)C).

EXAMPLE 4

Synthesis of isosorbide bis-β-acetoacetate

In a three-necked flask, a mixture of 73.05 g (0.5 mole) of isosorbide and 237.33 g (1.5 mole) of tert-butyl acetoacetate was heated at 100° C. with stirring until dissolution of the solids. The resulting solution was heated to 130° C. and then slowly (1.5 h) heated further to 150° C., and kept at this temperature for another 1.5 h. The tert-butyl alcohol formed during the reaction was distilled off: after 3 h 71.0 g (1.92 eq) had been collected, and the temperature was then lowered to 100° C. The excess of tert-butyl acetoacetate was distilled off under reduced pressure, while the temperature was slowly raised to 130° C. In this way, 70.1 g (0.44 mole) of tert-butyl acetoacetate was recovered. The residue, a viscous liquid, mainly consisted of isosorbide bis-acetoacetate (>90%), with only minor amounts of tert-butyl acetoacetate, isosorbide mono-acetoacetate and isosorbide.

$^{13}$C NMR (δ in ppm, CDCl$_3$): 30.03/30.17 (—CH$_3$), 49.70 (CO—CH$_2$—CO), 70.41/70.47 (—CH$_2$O—), 74.75+78.53+80.73+85.78 (—CH—O), 166.36/166.50 (O—C=O), 200.38/200.38 (H$_3$C—C=O).

EXAMPLE 5

Synthesis of isosorbide bis-β-aminocrotonate

Isosorbide bis-acetoacetate (see example 4), 20.05 g (64 mmole) in 125 ml of isopropanol was stirred at 30–40° C. until homogenisation. Ammonia was bubbled through the stirred mixture. After one hour the mixture turned yellow and after one more hour a colourless solid began to precipitate. After 5 hours, the solid was collected by filtration. Residual isopropanol was removed by drying one P$_2$O$_5$ in vacuo. Yield: 18.8 g (95%) of the title compound. Melting point: 160–162° C. $^{13}$C NMR (b in ppm, CDCl$_3$): 22.32/22.36 (—CH$_3$); 70.10+72.43 (—CH$_2$O—), 73.87+76.68+81.09+86.34 (—CH—O), 83.14/83.23 (—CH=C), 160.91+160.96 (C=C—N), 168.99+169.17 (C=O).

Decomposition Rate of Isosorbide bis-β-aminocrotonate

The rate of decomposition (ammonia release) of isosorbide bis-β-aminocrotonate was measured as follows: 1 g of sample was weighed into a boiling tube. At the top of the inside of the tube a red litmus paper was secured using cotton wool. The tube was suspended in an oil bath at room temperature. The oil bath was heated at a rate of 2° C. per min. At 5 minute intervals the litmus paper was observed for any colour change. The temperature and time interval at which the colour started to turn blue were noted. For the title compound, the litmus paper turned blue after 50 minutes at 125 ° C. For a comparable prior art compound, i.e. butyleneglycol bis-β-aminocrotonate, the litmus paper turned blue after 25 minutes at 81° C.

EXAMPLE 6

Test Results

The performance of PVC compounds stabilised by the compounds described in examples 1–5 was tested. The results are given in tables 1–4.

TABLE 1

Heat stability of rigid PVC (compound A) stabilised by the compounds of example 1 (sorbitol(AcAc)$_{3-4}$) and example 2 (lactitol(AcAc)$_6$)

|  | heat-stability (minutes) | Wb (%) | Yi (%) |
| --- | --- | --- | --- |
| blanc | 32.1 | 30.3 | 20.2 |
| sorbitol(AcAc)$_4$ 0.4 phr | 39.6 | 49.8 | 13.0 |
| lactitol(AcAc)$_6$ 0.4 phr | 42.0 | 35.1 | 18.6 |
| lactitol(AcAc)$_6$ 0.6 phr | 46.5 | 42.2 | 15.9 |

TABLE 2

Heat stability of flexible PVC (compound C) stabilised by the compound of example 3 (lactitol(AcAc)$_3$)

|  | heat-stability (minutes) | Wb (%) | Yi (%) |
| --- | --- | --- | --- |
| blanc | 17.7 | 50.7 | 12.5 |
| lactitol(AcAc)$_3$ 0.1 phr | 24.9 | 48.0 | 14.2 |
| lactitol(AcAc)$_3$ 0.3 phr | 27.2 | 41.3 | 16.7 |

TABLE 3

Heat stability of PVC (compound D) stabilised by the compound of example 1 (sorbitol(AcAc)$_4$) with or without sorbitol or lactitol

|  | heat-stability (minutes) | Yi (%) |
| --- | --- | --- |
| blanc | 20.3 | 50.8 |
| dipentaerythritol 0.3 phr | 43 | 74.9 |

TABLE 3-continued

Heat stability of PVC (compound D) stabilised by
the compound of example 1 (sorbitol(AcAc)$_4$) with or without
sorbitol or lactitol

| | heat-stability (minutes) | Yi (%) |
|---|---|---|
| sorbitol 0.3 phr | 40.5 | 92.9 |
| sorbitol 0.3 phr + sorbitol(AcAc)$_4$ 0.3 phr | 42.0 | 74.3 |
| lactitol 0.3 phr | 40.5 | 91.6 |
| lactitol 0.3 phr + sorbitol(AcAc)$_4$ 0.3 phr | 41.1 | 75.3 |

TABLE 4

Heat stability of PVC (compound D) stabilised by the compound
of example 5 (isosorbide bis-β-aminocrotanoate: IBAC)
with sorbitol

| | heat-stability (minutes) | Yi (%) |
|---|---|---|
| blanc | 20.3 | 50.8 |
| sorbitol 0.3 phr | 40.5 | 92.9 |
| sorbitol 0.4 phr + IBAC 0.2 phr | 31.5 | 61.6 |

EXAMPLE 7

Transesterification of butyl lactate to lactic acid 2,
2,6,6-tetramethyl-4-piperidyl ester In a round-bottomed flask equipped with a magnetic stirrer and a Dean Stark apparatus, 10.0 g butyl lactate (68.4 mmol), 10.75 g 2,2,6,6-tetramethyl-4-piperidinol (68.4 mmol) and 1 g Ti(OBu)$_4$ were added and butanol was distilled off at 135–140° C. A light brown waxy material was obtained. Yield: 13.5 g (85%).

Synthesis of 2-(acetoacetyloxy)-propionic acid 2,2,
6,6-tetramethyl-4-piperidyl ester Lactic acid 2,2,6,6-tetramethyl-4-piperidyl ester (5 g, 21.8 mmol) was dissolved in 100 ml of toluene. At reflux temperature, 3.1 g (21.8 mmol) of 2,2,6-trimethyl-4H-1,3-dioxine-4-one was added dropwise. After 3 hours at reflux, the solvent was distilled of in vacuo. A viscous residue was left. Yield 4.8 g (70%).

What is claimed is:

1. A process for stabilising thermoplastic polymers, comprising incorporating into a polymer-producing mixture a β-ketoester or the corresponding β-enamine represented by formulae 1 and 2, respectively:

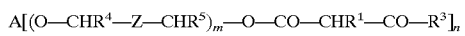  1

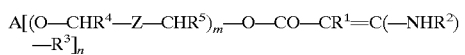  2 wherein:
A is the residue of an alcohol or polyol selected from hydroxyalkanoic acid esters, sugars and their glycosides, sugar alcohols and their dehydration products, sugar acids and their esters, and oligosaccharides;
m is an integer number from 0 up to 6;
n is a number from 1 up to the total number of hydroxyl groups in the polyol;
R$^1$ is hydrogen, C$_1$–C$_8$ alkyl, C$_3$–C$_8$ alkenyl or cycloalkyl (alkyl) or C$_6$–C$_8$ aryl or aralkyl;
R$^2$ is hydrogen, C$_1$–C$_6$ alkyl, C$_2$–C$_6$ hydroxyalkyl or C$_3$–C$_6$ alkenyl;
R$^3$ is C$_1$–C$_{18}$ alkyl, alkoxy or alkylamino, C$_3$–C$_{18}$ alkenyl, alkanoylmethyl, alkoxycarbonylmethyl or cycloalkyl(alkyl), C$_6$–C$_{18}$ aryl, aryloxy, arylamino, aralkyl, aralkoxy or aralkylamino, or C$_8$–C$_{18}$ aroylmethyl, aryloxycarbonylmethyl or arylcarbamoylmethyl;
R$^4$ and R$^5$ are independently hydrogen or methyl; and
Z is a direct bond, CH$_2$, CHOH, CH—O—CO—CHR$^1$—CO—R$^3$ or CH—O—CO—CH=C(NHR$^2$)—R$^3$.

2. A process according to claim 1, wherein said sugar alcohol is a monosaccharide alcohol.

3. A process according to claim 2, wherein said β-ketoester is sorbitol polyacetoacetate.

4. A process according to claim 1, wherein said sugar alcohol dehydration product is a monosaccharide alcohol dehydration product.

5. A process according to claim 4, wherein said enamine is isosorbide bis-β-aminocrotonate.

6. A process according to claim 1, wherein said oligosaccharide is an oligofructose or a cyclodextrin.

7. A process according to claim 1, wherein R$^3$ is C$_1$–C$_4$ alkyl, or phenyl, benzyl or phenethyl optionally substituted by hydroxy and/or C$_1$–C$_4$ alkyl, wherein, if n>1, each R$^3$ may be different.

8. A process according to claim 1, wherein said hydroxyalkanoic ester is a C$_1$–C$_{18}$ alkyl, optionally substituted C$_6$–C$_{18}$ (alk)aryl or optionally substituted 4-piperidyl ester of lactic acid, citric acid, ascorbic acid or sugar acids.

9. A process according to claim 1, wherein said thermoplastic polymer is selected from chlorinated polymers, polyalkenes (polyethene, polypropene) and halogenated rubbers.

10. A process according to any one of claims 1–9, comprising incorporating 0.001–5 phr of the β-ketoester or enamine into said polymer-producing mixture.

11. A process according to any one of claims 1–10, wherein said thermoplastic polymer is selected from chlorinated polymers, polyalkenes (polyethene, polypropene) and halogenated rubbers, especially PVC.

12. A premix according to claim 10, wherein said polyol is selected from sorbitol, mannitol, sorbitan, galactitan, lactitol, inlulin, tris(hydroxyethyl)isocyanurate, di(pentaerythritol, trismethylolpropane and mixtures thereof.

13. A premix according to claim 12, wherein said metal alkanoate is selected from alkali metal, alkaline earth metal, aluminium, zinc, tin and lead salts of C$_4$–C$_{20}$ alkanoic acids.

14. A premix according to claim 10, wherein said stabilisers further comprise sterically hindered phenolic compounds, hindered amine light stabilisers, other UV stabilisers, organophosphites and/or epoxides.

15. A β-diketoester or its enamine suitable for stabilising thermoplastic polymers, represented by formulae 3 and 4, respectively,

  3

  4 wherein:
A is the residue of a dehydration product of a sugar alcohol,
R$^1$ is hydrogen, C$_1$–C$_8$ alkyl, C$_3$–C$_8$ alkenyl or cycloalkyl (alkyl) or C$_6$–C$_8$ aryl or aralkyl;

$R^2$ is hydrogen, $C_1$–$C_6$ alkyl, $C_2$–$C_6$ hydroxyalkyl or $C_3$–$C_6$ alkenyl; and $R^3$ is $C_1$–$C_{18}$ alkyl, alkoxy or alkylamino, $C_3$–$C_{18}$ alkenyl, alkanoylmethyl, alkoxy-carbonylmethyl or cycloalkyl(alkyl), $C_6$–$C_{18}$ aryl, aryloxy, arylamino, aralkyl, aralkoxy or aralkylamino, or $C_8$–$C_{18}$ aroylmethyl, aryloxycarbonylmethyl or arylcarbamoylmethyl.

* * * * *